(12) United States Patent
Powell et al.

(10) Patent No.: US 9,353,478 B2
(45) Date of Patent: *May 31, 2016

(54) BIOMASS TREATMENT FOR HYDROTHERMAL HYDROCATALYTIC CONVERSION

(71) Applicant: SHELL OIL COMPANY, Houston, TX (US)

(72) Inventors: Joseph Broun Powell, Houston, TX (US); Juben Nemchand Chheda, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/574,530

(22) Filed: Dec. 18, 2014

(65) Prior Publication Data

US 2015/0167237 A1    Jun. 18, 2015

Related U.S. Application Data

(60) Provisional application No. 61/917,422, filed on Dec. 18, 2013.

(51) Int. Cl.
| | |
|---|---|
| *C07C 27/00* | (2006.01) |
| *D21C 11/00* | (2006.01) |
| *C07C 29/132* | (2006.01) |
| *C13K 1/02* | (2006.01) |
| *C07C 1/24* | (2006.01) |
| *C07G 1/00* | (2011.01) |
| *C10G 1/06* | (2006.01) |
| *C10G 3/00* | (2006.01) |
| *C08H 8/00* | (2010.01) |

(52) U.S. Cl.
CPC .............. *D21C 11/0028* (2013.01); *C07C 1/24* (2013.01); *C07C 29/132* (2013.01); *C07G 1/00* (2013.01); *C08H 8/00* (2013.01); *C10G 1/065* (2013.01); *C10G 3/42* (2013.01); *C10G 3/50* (2013.01); *C13K 1/02* (2013.01); *C10G 2300/1014* (2013.01); *C10G 2300/202* (2013.01); *C10G 2300/205* (2013.01); *C10G 2300/4081* (2013.01); *Y02P 30/20* (2015.11)

(58) Field of Classification Search
CPC ........ C07C 1/24; C07C 27/00; C07C 29/132; C08G 1/00; C08G 3/42

USPC ........................................... 658/861; 568/861
See application file for complete search history.

(56) References Cited

U.S. PATENT DOCUMENTS

| | | | |
|---|---|---|---|
| 8,729,324 B2 | 5/2014 | Powell et al. | |
| 2008/0300435 A1 | 12/2008 | Cortright et al. | |
| 2010/0236988 A1 | 9/2010 | Gabrielov et al. | |
| 2012/0151827 A1 | 6/2012 | Powell et al. | |
| 2012/0152836 A1 | 6/2012 | Powell et al. | |
| 2012/0317872 A1 | 12/2012 | Powell et al. | |
| 2012/0317873 A1* | 12/2012 | Johnson .................... | C10L 5/44 44/307 |
| 2013/0109896 A1 | 5/2013 | Powell et al. | |
| 2013/0152457 A1 | 6/2013 | Powell et al. | |
| 2013/0152458 A1 | 6/2013 | Powell et al. | |
| 2014/0005444 A1 | 1/2014 | Komplin et al. | |
| 2014/0005445 A1 | 1/2014 | Komplin et al. | |
| 2014/0117275 A1 | 5/2014 | Powell et al. | |
| 2014/0117276 A1 | 5/2014 | Powell et al. | |
| 2014/0117277 A1 | 5/2014 | Powell et al. | |
| 2014/0121418 A1 | 5/2014 | Powell et al. | |
| 2014/0121419 A1 | 5/2014 | Powell et al. | |
| 2014/0121420 A1 | 5/2014 | Powell et al. | |
| 2014/0166221 A1 | 6/2014 | Powell et al. | |
| 2014/0174432 A1 | 6/2014 | Powell | |
| 2014/0174433 A1 | 6/2014 | Powell | |
| 2015/0167240 A1 | 6/2015 | Powell et al. | |
| 2015/0184081 A1 | 7/2015 | Powell et al. | |

FOREIGN PATENT DOCUMENTS

WO    2013120492    8/2013

OTHER PUBLICATIONS

International Search Report Apr. 1, 2015 of PCT/US2014/071064 filed Dec. 18, 2014.

* cited by examiner

*Primary Examiner* — Porfirio Nazario Gonzalez
*Assistant Examiner* — Kofi Adzamli (57) ABSTRACT

A selective removal of chlorine and phosphorus that are detrimental to subsequent hydrothermal hydrocatalytic conversion from the biomass feed prior to carrying out catalytic hydrogenation/hydrogenolysis/hydrodeoxygenation of the biomass in a manner that does not reduce the effectiveness of the hydrothermal hydrocatalytic treatment while minimizing the amount of water used in the process is provided.

14 Claims, 1 Drawing Sheet

BIOMASS TREATMENT FOR HYDROTHERMAL HYDROCATALYTIC CONVERSION

PRIORITY CLAIM

The present non-provisional application claims priority from U.S. Provisional Application 61/917,422, filed Dec. 18, 2013, the entire disclosure of which is hereby incorporated by reference.

FIELD OF THE INVENTION

The invention relates to treatment of biomass for the hydrothermal hydrocatalytic treatment in the production of higher hydrocarbons suitable for use in transportation fuels and industrial chemicals from biomass. More specifically, the invention relates to removal of phosphorus and chlorine from the biomass for an effective biomass hydrothermal hydrocatalytic conversion.

BACKGROUND OF THE INVENTION

A significant amount of attention has been placed on developing new technologies for providing energy from resources other than fossil fuels. Biomass is a resource that shows promise as a fossil fuel alternative. As opposed to fossil fuel, biomass is also renewable.

Biomass may be useful as a source of renewable fuels. One type of biomass is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose. Hemicellulose and pectin are typically found in abundance, but cellulose is the predominant polysaccharide and the most abundant source of carbohydrates. However, production of fuel from cellulose poses a difficult technical problem. Some of the factors for this difficulty are the physical density of lignocelluloses (like wood) that can make penetration of the biomass structure of lignocelluloses with chemicals difficult and the chemical complexity of lignocelluloses that lead to difficulty in breaking down the long chain polymeric structure of cellulose into carbohydrates that can be used to produce fuel. Another factor for this difficulty is the nitrogen compounds and sulfur compounds contained in the biomass. The nitrogen and sulfur compounds contained in the biomass can poison catalysts used in subsequent processing.

Most transportation vehicles require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier.

Currently, bio-based feedstocks such as biomass provide the only renewable alternative for liquid transportation fuel. Unfortunately, the progress in developing new technologies for producing liquid biofuels has been slow in developing, especially for liquid fuel products that fit within the current infrastructure. Although a variety of fuels can be produced from biomass resources, such as ethanol, methanol, and vegetable oil, and gaseous fuels, such as hydrogen and methane, these fuels require either new distribution technologies and/or combustion technologies appropriate for their characteristics. The production of some of these fuels also tends to be expensive and raise questions with respect to their net carbon savings. There is a need to directly process biomass into liquid fuels, amenable to existing infrastructure.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). Further, it is a challenge to minimize generation of waste products that may require treating before disposal and/or catalyst deactivation by poisons.

SUMMARY OF THE INVENTION

It was found desirable to remove chlorine and phosphorus from the biomass feed prior to carrying out catalytic hydrogenation/hydrogenolysis/ hydrodeoxygenation of the biomass in a manner that does not reduce the effectiveness of the hydrothermal hydrocatalytic treatment while minimizing the amount of water used in the process.

In one embodiment, a method for selective removal of chlorine and phosphorus from cellulosic biomass solids is provided, said method comprising a plurality of vessels:
   a. providing each of said vessels with one of detrimental species-containing cellulosic biomass solids;
   b. introducing a quantity of a base solution having a pH of greater than 9 from an inlet into a first vessel of said plurality of vessels containing said detrimental species-containing cellulosic biomass solids at a temperature in the range of about 0° C. to about 60° C.;
   c. repeating step (b) for a second vessel of said plurality of vessels;
   d. introducing a quantity of aqueous solution having a pH of at most 8 from an inlet into said first vessel of said plurality of vessels treated according to step (b) thereby discharging the basic water effluent;
   e. repeating step (d) for the second vessel of said plurality of vessels treated according to step (c);
   f. introducing a quantity of gas or organic solution from an inlet into the first vessel of said plurality of vessels treated according to step (d) and discharging the aqueous effluent;
   g. repeating step (f) for the second vessel of said plurality of vessels treated according to step (e);
   h. recycling at least a portion of the discharged aqueous effluent as a portion of the base solution;
   i. transferring at least a portion of the biomass treated according to steps (f) and (g) to a digestion and/or reaction vessel;
   j. wherein at least 2 of the vessels are undergoing at least one of the steps (b) through (i) at the same time; and
   k. wherein the amount of the total basic water effluent from the plurality of vessels is in the range of from about 3 parts to about 0.5 parts relative to about 1 part of detrimental species—containing cellulosic biomass solids (dry basis).

In yet another embodiment, in the digestion and/or reaction zone of the above methods, the treated cellulosic biomass is contacted with a hydrothermal hydrocatalytic catalyst in the presence of hydrogen and a digestion solvent thereby producing an intermediate oxygenated product stream comprising oxygenated hydrocarbons and water; and at least a portion of the water is separated and recycled to form at least a portion of the aqueous solution.

In yet another embodiment, in the digestion and/or reaction zone in the above methods, the treated cellulosic biomass is contacted with a hydrothermal hydrocatalytic catalyst in the presence of hydrogen and a digestion solvent thereby producing an intermediate oxygenated product stream; at least a portion of the oxygenated intermediate product stream is converted to a hydrocarbon product stream comprising hydrocarbons and water; and at least a portion of the water is separated and recycled to form at least a portion of the aqueous solution. The oxygenated intermediate product steam may comprise oxygenated hydrocarbons and water, and at least a portion of the water maybe separated and recycled to form at least a portion of the aqueous solution.

The features and advantages of the invention will be apparent to those skilled in the art. While numerous changes may be made by those skilled in the art, such changes are within the spirit of the invention.

BRIEF DESCRIPTION OF THE DRAWING

This drawing illustrates certain aspects of some of the embodiments of the invention, and should not be used to limit or define the invention.

DETAILED DESCRIPTION OF THE INVENTION

In one embodiment, the invention relates to selective removal of chlorine and phosphorus, from a cellulosic biomass solids. Any suitable (e.g., inexpensive and/or readily available) type of lignocellulosic biomass can be used. Suitable lignocellulosic biomass can be, for example, selected from, but not limited to, wood, forestry residues, agricultural residues, herbaceous material, municipal solid wastes, pulp and paper mill residues, and combinations thereof. Thus, in some embodiments, the biomass can comprise, for example, corn stover, straw, bagasse, miscanthus, sorghum residue, switch grass, duckweed, bamboo, water hyacinth, hardwood, hardwood chips, hardwood pulp, softwood, softwood chips, softwood pulp, and/or combination of these feedstocks. The biomass can be chosen based upon a consideration such as, but not limited to, cellulose and/or hemicelluloses content, lignin content, growing time/season, growing location/transportation cost, growing costs, harvesting costs and the like. These cellulosic biomass solids contain chlorine and phosphorus species that are detrimental to catalysts or equipment used in the hydrothermal hydrocatalytic treatment of the biomass ("detrimental species"). Hence, it is desirable to at least in part remove phosphorus and chlorine species from the cellulosic biomass solids before the hydrothermal hydrocatalytic treatment of biomass.

The oxygenated hydrocarbons produced from the hydrothermal hydrocatalytic process are useful in the production of higher hydrocarbons suitable for use in transportation fuels and industrial chemicals from biomass. The higher hydrocarbons produced are useful in forming transportation fuels, such as synthetic gasoline, diesel fuel, and jet fuel, as well as industrial chemicals. As used herein, the term "higher hydrocarbons" refers to hydrocarbons having an oxygen to carbon ratio less than the oxygen to carbon ratio of at least one component of the biomass feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (i.e., oxygen sulfur, phosphorus, or nitrogen) and thus the term "hydrocarbon" may also include substituted hydrocarbons. As used herein, the term "soluble carbohydrates" refers to monosaccharides or polysaccharides that become solubilized in a digestion process.

Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. Further the process should maximize product yield while minimizing waste products. These basic requirements lead to a number of secondary issues that collectively present an immense engineering challenge that has not been solved heretofore.

Further, the removal of these detrimental species is complicated by the sensitivity of the catalysts for the hydrothermal hydrocatalytic treatment to the reaction conditions. Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). For example, too much water from a wash process can dilute the reaction stream and require removal of larger amounts of water from the process and may further lead to stress on the catalyst used in the process. Further, removal of water at a later stage by thermally separating the water will require a large amount of energy. It is also desirable to recycle the wash water to minimize or eliminate the need for other water inputs to the process.

In further embodiment, the invention relates recycling the water used to wash the biomass and to minimizing the amount of waste water generated in the process. The invention balances the competing advantage of selective removal of chlorine and phosphorus, from cellulosic biomass solids while not reducing the effectiveness of the hydrothermal hydrocatalytic treatment while minimizing the amount of water used in the process. Applicants have found that washing the biomass with base solution at low temperature effectively removes at least a portion of the chlorine and phosphorus the biomass without removal of carbohydrates. However a large amount of water required to remove the chlorine and phosphorus species also hinders and/or creates more process water that requires more water removal and disposals. The process of the invention provides effective solutions to these problems.

It is also important in the wash process to prevent the hydrolysis of wood and loss of carbohydrate to the wash effluent (or aqueous solution effluent). Thus it is preferable to maintain the treatment of the biomass to at most about 60° C. The loss of carbohydrate is preferably less than 10% by weight, more preferably less than 5% by weight, even more preferably less than 2% by weight based on the carbohydrates present in the biomass (dry basis).

Prior to treatment, the untreated biomass can be reduced in size (e.g., chopping, crushing or debarking) to a convenient size and certain quality that aids in moving the biomass or mixing and impregnating the chemicals from digestive solvent. Thus, in some embodiments, providing biomass can comprise harvesting a lignocelluloses-containing plant such as, for example, a hardwood or softwood tree. The tree can be subjected to debarking, chopping to wood chips of desirable thickness, and washing to remove any residual soil, dirt and the like.

It is preferable to render the biomass feed (wood chips or other) free of entrained air, and densified to insure the feedstock will sink in water or solvent, vs. float (pre-conditioning). Floating can occur if the feed is allowed to dry during storage, upon which air may enter pores and be transported into the process.

Densification via impregnation with water or solvent may be effected by soaking in water or solvent. Pressurization of the water or solvent will force liquid into pores. One of the most effective ways to drive gas (air or non-condensibles) out of the pore of the biomass is to contact the biomass with solvent vapor, most preferable water vapor or steam.

Typically, this is done by supplying low pressure steam (nominal 1-2 atmospheres above ambient pressure) to the bottom of a storage bin, and allowing the steam or solvent vapor to travel upwards through the bin of solids, to drive out air or entrained gas. Contacting of water or solvent vapor at a temperature above the biomass temperature results in condensation of liquid water or vapor in the pores of the biomass, driving gas out of the pores. This saturates and densifies the biomass such that it now has a density greater than water or solvent, and therefore sinks when added to liquid water or solvent during the wash process.

The time and duration of the steaming should be controlled such that the temperature of the biomass does not exceed about 60 degrees centigrade for an extended period of time. Specifically, one can supply steam at temperatures above 100 degrees centigrade (the boiling point of water), to biomass initially at ambient temperature (below about 35 degrees centigrade), for a period of time such that the final temperature of the biomass does not exceed about 60 degrees centigrade, or if temperature above 60 degree centigrade, the exposure at this temperature is limited to less than 60 minutes, preferably less than 30 minutes, and most preferably less than about 10 minutes. By minimizing the exposure to temperatures above 60° C., hydrolysis and degradation of carbohydrate components is minimized, and loss of these components to the water and/or acid and base wash process steps can be minimized to less than 5% of the carbohydrate portion of the biomass, most preferably less than 1%.

In the process of the invention, a plurality of vessels that can be 2 or more vessels are used in parallel. The plurality of vessels are used in parallel where at least 2 of the plurality of vessels are undergoing at least one of the steps of the process at the same time. There may be n vessels where n can be any integer. In some embodiments, the number of vessels may be an integer from 2 to 20, preferably 2 to 10. In some embodiment, the number of vessels maybe an integer from 3 to 6. The vessel can be in any shape that include, for example, vertical, horizontal, incline, and may include bends, curves or u shape. The vessel will further have at least one inlet and at least one outlet.

The detrimental species-containing cellulosic biomass solids is provided (or introduced) in to a first (treatment) vessel. This process is repeated for the second (treatment) vessel. This process can be repeated for 3, 4, 5, 6, 7, 8, 9, 10, or n vessels.

In one embodiment, a base solution having a pH of greater than 9, preferably having a pH of at most 13, more preferably having a pH of at least 10, more preferably having a pH in the range of 10 to 13, may be introduced to the vessel containing the cellulosic biomass solids at a temperature in the range of 0° C. to 60° C., preferably in the range of 10° C. to 45° C., producing a basic cellulosic biomass solids. The inlet may be the same inlet as the biomass solids introduction or a separate, second inlet to the treatment vessel. This step is carried out with the first vessel and repeated for a second vessel. The step can be carried out to n number of vessels, that may be third, fourth, fifth, sixth, seventh, eighth, ninth, tenth, etc. up to n vessels.

After the base solution introduction, an aqueous solution having a pH of at least 5 to at most 9 is introduced from an inlet to the basic cellulosic biomass solids-containing vessel producing treated (or base washed in such embodiment) cellulosic biomass solids having reduced detrimental species content compared to the detrimental species-containing cellulosic and a basic water effluent. The inlet may be the same inlet as the biomass solids introduction, the base solution inlet, or a separate, second or third inlet to the treatment vessel. The basic water effluent and the treated cellulosic biomass solids may be removed from the treatment vessel from the same outlet or a separate, second, outlet. This step is carried out with the first vessel and repeated for a second vessel. The step can be carried out to n number of vessels, that may be third, fourth, fifth, sixth, seventh, eighth, ninth, tenth, etc. up to n vessels.

The base wash is carried out so that the amount of the total basic water effluent from the plurality of treatment vessels is in the range of about 3 parts to about 0.5 parts, preferably in the range of about 2 parts to about 1 part relative to the cellulosic biomass solids (dry basis) charged to the treatment step, based on weight. The basic water effluent and any aqueous effluent that is not recycled can be disposed individually or combined.

After introduction of the aqueous solution, a gas stream or an organic solvent solution is introduced to the vessel containing the washed cellulosic biomass solids, producing a pretreated cellulosic biomass solids with reduced water content compared to the water washed cellulosic biomass solids and an aqueous effluent. The inlet may be the same inlet as the biomass solids introduction, the base solution inlet, the aqueous solution inlet or a separate, second, third or fourth inlet to the treatment vessel. The aqueous effluent and the pretreated cellulosic biomass solids may be removed from the treatment vessel from the same outlet or a separate, second or third, outlet. In this water displacement step, the water content is reduced by at least by 5% by volume, preferably at least by 25% by volume, more preferably at least by 50% by volume, based on the liquid constituent of the water washed cellulosic biomass solids. This step is carried out with the first vessels and repeated for a second vessel. The step can be carried out to n number of vessels, that may be third, fourth, fifth, sixth, seventh, eighth, ninth, tenth, etc. up to n vessels.

The pretreated cellulosic biomass solids is discharged from an outlet of the treatment vessel, then transferred to a digestion and/or reaction zone. This step is carried out with the first vessels and repeated for a second vessel. The step can be carried out to n number of vessels, that may be third, fourth, fifth, sixth, seventh, eighth, ninth, tenth, etc. up to n vessels.

At least a portion of the aqueous effluent is recycled to produce base solution and/or aqueous solution.

At least a portion of the aqueous effluent is recycled to produce base solution, and/or aqueous solution. For example, at least a first portion of the aqueous effluent is recycled to produce base solution, and at least a second portion of the aqueous effluent is recycled as an aqueous solution.

The pretreated cellulosic biomass solids is discharged from an outlet of the treatment vessel, then transferred to a digestion and/or reaction zone. This step is carried out with the first vessel and repeated for a second vessel. The step can be carried out to n number of vessels, that may be third, fourth, fifth, sixth, seventh, eighth, ninth, tenth, etc. up to n vessels.

The above steps may be carried out in parallel in multiple vessels, each vessels undergoing at least one of the steps, thus increasing the efficiency of the wash process.

The step can be carried out to n number of vessels, that may be third, fourth, fifth, sixth, seventh, eighth, ninth, tenth, etc. up to n vessels as long as at least 2 of the vessels are undergoing at least one of the steps at the same time.

The use of recycle treatment water and parallel treatment vessels, as described in the present invention, is effective to produce an effluent separated from the biomass which contains a maximum concentrations of the detrimental removed components, in the restricted amounts of water treatment allowed. The amounts of water prescribed will typically correspond to the natural water content of the biomass feedstock, augmented by any water which can be made in process conversion steps such as reaction of biomass with hydrogen, with zero or minimal use of additional water from another source. The amount of additional water required is thus restricted to less than 50% of the biomass feed (dry basis), and hence would represent less than a third of the typical amount of additional water employed for similar processing in the manufacture of, for example, pulp used to make paper. Preferably, the amount of additional makeup water above the water naturally present in the biomass feed, and made in the process, is zero.

The base solution may contain an inorganic base such as, for example, KOH, NaOH and ammonia. The base content of the base solution is preferably less than 5 Normal and at least 0.01 Normal. The base concentration is preferably from about 0.1 to about 5 Normal.

Preferably, chlorine is reduced by at least 50%, at least 55%, at least 60%, and at least 75%. Preferably phosphorus is reduced by at least 75wt%, at least 80%, at least 85%, at least 90%, at least 95%, even at least 98% or essentially completely. The term "essentially completely" means the specie is completely removed within the detection limit or within statistical significance or within measurement errors At least a portion of the treated cellulosic biomass solids is provided to a digestion and/or reaction zone (collectively referred to as "hydrothermal hydrocatalytic reaction zone") for further processing. This zone may be conducted in a single step or in multiple steps or vessels as described below.

Figure 1:
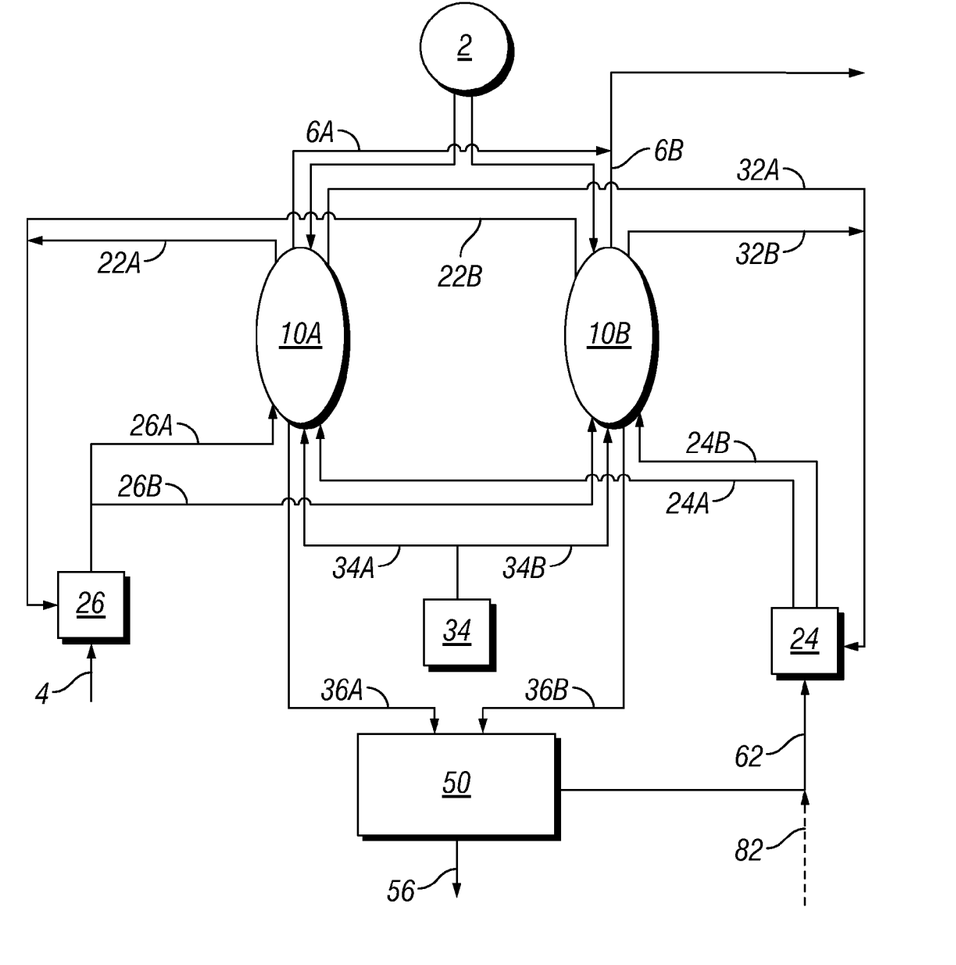
FIG. 1 is a schematically illustrated block flow diagram of an embodiment of a process of this invention.

In reference to FIG. 1, in one embodiment of the invention process, detrimental species-containing cellulosic biomass solids 2 is introduced into first vessel 10A. An base solution 26A having a pH of greater than 9, at a temperature in the range of 0° C. to 60° C. is introduced into the first vessel 10A ("base wash step") thereby producing an base washed cellulosic biomass solids. The base content in the base solution adjusted by dilution of base 4 by adding an aqueous solution that may be an aqueous effluent from the process (such as 22A or 22B) to make stream 26A and/or 26B as shown. The base solution may optionally be placed in a reservoir 26 and used as necessary for each treatment vessels. Then, an aqueous solution 24A having a pH of at least 5 to at most 9 is introduced to the base washed cellulosic biomass solids in the vessel 10A ("water rinse step") optionally from an aqueous solution reservoir 24, thereby producing water washed cellulosic biomass solids having at least partially reduced phosphorus and chlorine content compared to the detrimental species-containing cellulosic biomass solids and a basic effluent 6A. Any rinse water from 10A that are no longer basic (for example, having a pH of at most 9) may be made basic and used as the base solution. Then, a gas and/or an organic solvent 34A form an optional gas or organic solvent reservoir 34 is passed through said water washed cellulosic biomass solids, in the first vessel 10A ("water displacement step") thereby producing a pretreated cellulosic biomass solids 36A with reduced water content compared to the water washed cellulosic biomass solids and separated aqueous effluent 32A. In this water displacement step, the water content is reduced by at least by 5% by volume, preferably at least by 25% by volume, more preferably at least by 50% by volume, based on the liquid constituent of the water washed cellulosic biomass solids The above steps are also repeated for the second vessel in a similar manner to the first vessel. The detrimental species-containing cellulosic biomass solids 2 is introduced into the second vessel 10B. An base solution 26B having a pH of greater than 9, at a temperature in the range of 0° C. to 60° C. is introduced into the first vessel 10B ("base wash step") thereby producing a base washed cellulosic biomass solids. Then, an aqueous solution 24B having a pH of at least 5 to at most 9 is introduced to the base washed cellulosic biomass solids in the vessel 10B ("water rinse step") optionally from an aqueous solution reservoir 24, thereby producing water washed cellulosic biomass solids having at least partially reduced phosphorus and chlorine content compared to the detrimental species-containing cellulosic biomass solids and a basic effluent 6B. Any rinse water from 10B that are no longer basic (for example, having a pH of at most 9) may be made basic and used as the base solution. Then, a gas and/or an organic solvent 34B form an optional gas or organic solvent reservoir 34 is passed through said water washed cellulosic biomass solids, in the second vessel 10B ("water displacement step") thereby producing a pretreated cellulosic biomass solids 36B with reduced water content compared to the water washed cellulosic biomass solids and separated aqueous effluent 32B.

The same steps for the first vessel and second vessel may be carried out optionally for the third vessel, fourth vessel, fifth vessel, sixth vessel, seventh vessel, eighth vessel, ninth vessel, tenth vessel, etc. up to n vessels. The total basic water effluent from plurality of vessels may comprise water initially present in the wet biomass feed and water generated in the process, with makeup water that is less than 50% of the biomass feed (dry basis).

The above steps may be carried out in parallel in multiple vessels, each vessels undergoing at least one of the steps, thus increasing the efficiency of the wash process.

At least a portion of the separated aqueous effluent is recycled via a recycle conduit to the second contact zone to form at least a portion of the aqueous solution 24. The pretreated cellulosic biomass is provided to digestion/reaction zone ("hydrothermal catalytic reaction zone or system") 50 that may have one or more units, that in at least one unit containing a hydrothermal hydrocatalytic catalyst that is capable of activating molecular hydrogen to produce an intermediate oxygenated product stream 56 containing oxygenated hydrocarbons and water in the presence of hydrogen. Water may be removed from the oxygenated hydrocarbon stream produced in the thermal catalytic zone and recycled via 62 to form at least a portion of the aqueous solution 24. At least a portion of the oxygenated hydrocarbon stream may be converted in a conversion zone (not shown in Figures) to a hydrocarbon product stream comprising hydrocarbons and water; and at least a portion of the water may be separated and recycled 82 to the as the aqueous solution 24. Water may be separated from the hydrocarbon or from the oxygenated hydrocarbon stream by conventional method including liquid/liquid separation, decanting, distillation, or flashing.

For the instant biofuels process, the minimization of fresh water usage is a key issue. However, due to biomass packing density being poor, at best 3 parts or more of bed volume of water are required to typically fill a bed for washing one part of biomass. In the invention process, the detrimental species is removed with less than 5 parts, preferably at most 2.5 parts, more preferably at most 2 parts, even at most 1.5 parts of water for washing one part of biomass. It is preferred that for the removal process, only the water from the water in the biomass and water generated in the process For the hydrothermal catalytic reaction zone, the zone may have one or more vessels. In one embodiment in the digestion/reaction zone hydrolysis and hydrothermal hydrocatalytic reaction of the treated biomass is carried out in one or more vessels. These vessels may be digesters or reactors or combination thereof including a combination hydrothermal hydrocatalytic digestion unit.

In some embodiments, lignocellulosic biomass (solids) being added to the hydrothermal digestion unit or hydrothermal hydrocatalytic digestion unit may be pressurized before being added to the unit, particularly when the hydrothermal (hydrocatalytic) digestion unit is in a pressurized state. Pressurization of the cellulosic biomass solids from atmospheric pressure to a pressurized state may take place in one or more pressurization zones before addition of the cellulosic biomass solids to the hydrothermal (hydrocatalytic) digestion unit. Suitable pressurization zones that may be used for pressurizing and introducing lignocellulosic biomass to a pressurized hydrothermal digestion unit or hydrothermal hydrocatalytic digestion unit are described in more detail in commonly owned United States Patent Application Publications US20130152457 and US20130152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner The digestion and the hydrothermal hydrocatalytic reaction in the hydrothermal catalytic reaction zone (or digestion reaction zone) may be conducted separately, partially combined, or in situ.

In some embodiments, the digestion rate of cellulosic biomass solids may be accelerated in the presence of a liquid phase containing a digestion solvent. In some instances, the liquid phase may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures. One approach for addressing the degradation of soluble carbohydrates during hydrothermal digestion is to conduct an in situ catalytic reduction reaction process so as to convert the soluble carbohydrates into more stable compounds as soon as possible after their formation.

In certain embodiments, a slurry catalyst may be effectively distributed from the bottom of a charge of cellulosic biomass solids to the top using upwardly directed fluid flow to fluidize and upwardly convey slurry catalyst particulates into the interstitial spaces within the charge for adequate catalyst distribution within the digesting cellulosic biomass solids. Suitable techniques for using fluid flow to distribute a slurry catalyst within cellulosic biomass solids in such a manner are described in commonly owned United States Patent Application Publications US20140005445 and US20140005444 and incorporated herein by reference in its entirety. In addition to affecting distribution of the slurry catalyst, upwardly directed fluid flow may promote expansion of the cellulosic biomass solids and disfavor gravity-induced compaction that occurs during their addition and digestion, particularly as the digestion process proceeds and their structural integrity decreases. Methods of effectively distributing molecular hydrogen within cellulosic biomass solids during hydrothermal digestion is further described in commonly owned United States Patent Application Publications US20140174433 and US20140174432 and incorporated herein by reference in its entirety.

In another embodiment the hydrothermal hydrocatalytic digestion unit may be configured as disclosed in a co-pending United States Patent Application Publication. US20140117276 which disclosure is hereby incorporated by reference. In the digestion zone, the size-reduced biomass is contacted with the digestive solvent where the digestion reaction takes place. The digestive solvent must be effective to digest lignins.

In some embodiments, at least a portion of oxygenated hydrocarbons produced in the hydrothermal hydrocatalytic reaction zone are recycled within the process and system to at least in part from the in situ generated solvent, which is used in the biomass digestion process. Further, by controlling the degradation of carbohydrate in the hydrothermal hydrocatalytic reaction (e.g., hydrogenolysis process), hydrogenation reactions can be conducted along with the hydrogenolysis reaction at temperatures ranging from about 150° C. to 300° C. As a result, a separate hydrogenation reaction section can optionally be avoided, and the fuel forming potential of the biomass feedstock fed to the process can be increased. Further, it may be advantageous to use the in situ generated solvent as the organic solvent in the pretreatment.

In various embodiments, the fluid phase digestion medium in which the hydrothermal digestion and catalytic reduction reaction, in the hydrothermal hydrocatalytic reaction zone, are conducted may comprise an organic solvent and water. Although any organic solvent that is at least partially miscible with water may be used as a digestion solvent, particularly advantageous organic solvents are those that can be directly converted into fuel blends and other materials without being separated from the alcoholic component being produced from the cellulosic biomass solids. That is, particularly advantageous organic solvents are those that may be co-processed along with the alcoholic component during downstream processing reactions into fuel blends and other materials. Suitable organic solvents in this regard may include, for example, ethanol, ethylene glycol, propylene glycol, glycerol, phenolics and any combination thereof. In situ generated organic solvents are particularly desirable in this regard.

In some embodiments, the fluid phase digestion medium may comprise between about 1% water and about 99% water. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the fluid phase digestion medium may comprise about 90% or less water by weight. In other embodiments, the fluid phase digestion medium may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

In some embodiments, hydrothermal hydrocatalytic catalysts, which are capable of activating molecular hydrogen (e.g., hydrogenolysis catalyst) and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst may be deposited on a catalyst support that may not itself be catalytically active.

In some embodiments, the hydrothermal hydrocatalytic catalyst may comprise a slurry catalyst. In some embodiments, the slurry catalyst may comprise a poison-tolerant catalyst. As used herein the term "poison-tolerant catalyst" refers to a catalyst that is capable of activating molecular hydrogen without needing to be regenerated or replaced due to low catalytic activity for at least about 12 hours of continuous operation. Use of a poison-tolerant catalyst may be particularly desirable when reacting soluble carbohydrates derived from cellulosic biomass solids that have not had catalyst poisons removed therefrom. Catalysts that are not poison tolerant may also be used to achieve a similar result, but they may need to be regenerated or replaced more frequently than does a poison-tolerant catalyst.

In some embodiments, suitable poison-tolerant catalysts may include, for example, sulfided catalysts. In some or other embodiments, nitrided catalysts may be used as poison-tolerant catalysts. Sulfided catalysts suitable for activating molecular hydrogen and buffers suitable for use with such catalysts are described in commonly owned United States Patent Application Publications US20120317872, US20130109896, US20120317873 and US20140166221 each of which is incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise (a) sulfur and (b) Mo or W and (c) Co and/or Ni or mixtures thereof. The pH buffering agent, may be suitable be an inorganic salt, particularly alkali salts such as, for example, potassium hydroxide, sodium hydroxide, and potassium carbonate or ammonia. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be distributed in the cellulosic biomass solids using fluid flow. Illustrative techniques for catalyst sulfiding that may be used in conjunction with the methods described herein are described in United States Patent Application Publication US20100236988 and incorporated herein by reference in its entirety.

In various embodiments, slurry catalysts used in conjunction with the methods described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

In some embodiments, the catalysts used in conjunction with the processes described herein may be operable to generate molecular hydrogen. For example, in some embodiments, catalysts suitable for aqueous phase reforming (i.e., APR catalysts) may be used. Suitable APR catalysts may include, for example, catalysts comprising Pt, Pd, Ru, Ni, Co, or other Group VIII metals alloyed or modified with Re, Mo, Sn, or other metals such as described in United States Patent Publication US20080300435 and incorporated herein by reference in its entirety.

In some embodiments, the alcoholic component formed from the cellulosic biomass solids may be further reformed into a biofuel. Reforming the alcoholic component into a biofuel or other material may comprise any combination and sequence of further hydrogenolysis reactions and/or hydrogenation reactions, condensation reactions, isomerization reactions, oligomerization reactions, hydrotreating reactions, alkylation reactions, dehydration reactions, desulfurization reactions, and the like. The subsequent conversion reactions may be catalytic or non-catalytic. In some embodiments, an initial operation of downstream conversion may comprise a condensation reaction, often conducted in the presence of a condensation catalyst, in which the alcoholic component or a product derived therefrom is condensed with another molecule to form a higher molecular weight compound. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art. Additional disclosure regarding condensation reactions and catalysts suitable for promoting condensation reactions is provided hereinbelow.

In some embodiments, methods described herein may further comprise performing a condensation reaction on the alcoholic component or a product derived therefrom. In various embodiments, the condensation reaction may take place at a temperature ranging between about 5° C. and about 500° C. The condensation reaction may take place in a condensed phase (e.g., a liquor phase) or in a vapor phase. For condensation reactions taking place in a vapor phase, the temperature may range between about 75° C. and about 500° C., or between about 125° C. and about 450° C. For condensation reactions taking place in a condensed phase, the temperature may range between about 5° C. and about 475° C., or between about 15° C. and about 300° C., or between about 20° C. and about 250° C.

Each reactor vessel preferably includes an inlet and an outlet adapted to remove the product stream from the vessel or reactor. In some embodiments, the vessel in which at least some digestion occurs may include additional outlets to allow for the removal of portions of the reactant stream. In some embodiments, the vessel in which at least some digestion occurs may include additional inlets to allow for additional solvents or additives.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons. In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure.

In some embodiments, a single catalyst may mediate the transformation of the alcoholic component into a form suitable for undergoing a condensation reaction as well as mediating the condensation reaction itself. In other embodiments, a first catalyst may be used to mediate the transformation of the alcoholic component into a form suitable for undergoing a condensation reaction, and a second catalyst may be used to mediate the condensation reaction. Unless otherwise specified, it is to be understood that reference herein to a condensation reaction and condensation catalyst refers to either type of condensation process. Further disclosure of suitable condensation catalysts now follows.

In some embodiments, a single catalyst may be used to form a higher molecular weight compound via a condensation reaction. Without being bound by any theory or mechanism, it is believed that such catalysts may mediate an initial dehydrogenation of the alcoholic component, followed by a condensation reaction of the dehydrogenated alcoholic component. Zeolite catalysts are one type of catalyst suitable for directly converting alcohols to condensation products in such a manner. A particularly suitable zeolite catalyst in this regard may be ZSM-5, although other zeolite catalysts may also be suitable.

In some embodiments, two catalysts may be used to form a higher molecular weight compound via a condensation reaction. Without being bound by any theory or mechanism, it is believed that the first catalyst may mediate an initial dehydrogenation of the alcoholic component, and the second catalyst may mediate a condensation reaction of the dehydrogenated alcoholic component. Like the single-catalyst embodiments discussed previously above, in some embodiments, zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired.

In some embodiments, the condensation catalyst may comprise a basic catalyst comprising Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the basic catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the basic catalyst may comprise a mixed-oxide basic catalyst. Suitable mixed-oxide basic catalysts may comprise, for example, Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. In some embodiments, the condensation catalyst may further include a metal or alloys comprising metals such as, for example, Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Use of metals in the condensation catalyst may be desirable when a dehydrogenation reaction is to be carried out in concert with the condensation reaction. Basic resins may include resins that exhibit basic functionality. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a hydrotalcite material derived from a combination of MgO and $Al_2O_3$. In some embodiments, the condensation catalyst may comprise a zinc aluminate spinel formed from a combination of ZnO and $Al_2O_3$. In still other embodiments, the condensation catalyst may comprise a combination of ZnO, $Al_2O_3$, and CuO. Each of these materials may also contain an additional metal or alloy, including those more generally referenced above for basic condensation catalysts. In more particular embodiments, the additional metal or alloy may comprise a Group 10 metal such Pd, Pt, or any combination thereof.

In some embodiments, the condensation catalyst may comprise a basic catalyst comprising a metal oxide containing, for example, Cu, Ni, Zn, V, Zr, or any mixture thereof. In some or other embodiments, the condensation catalyst may comprise a zinc aluminate containing, for example, Pt, Pd, Cu, Ni, or any mixture thereof.

In some embodiments, the condensation catalyst may comprise a multi-functional catalyst having both an acidic functionality and a basic functionality. Such condensation catalysts may comprise a hydrotalcite, a zinc-aluminate, a phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the multi-functional catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and any combination thereof. In some embodiments, the multi-functional catalyst may include a metal such as, for example, Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a metal oxide containing Pd, Pt, Cu or Ni. In still other embodiments, the condensation catalyst may comprise an aluminate or a zirconium metal oxide containing Mg and Cu, Pt, Pd or Ni. In still other embodiments, a multi-functional catalyst may comprise a hydroxyapatite (HAP) combined with one or more of the above metals.

In some embodiments, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

In some embodiments, an acid catalyst may be used to optionally dehydrate at least a portion of the reaction product. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self-supporting, supported on an inert support or resin, or it may be dissolved in a fluid.

Various operations may optionally be performed on the alcoholic component prior to conducting a condensation reaction. In addition, various operations may optionally be performed on a fluid phase containing the alcoholic component, thereby further transforming the alcoholic component or placing the alcoholic component in a form more suitable for taking part in a condensation reaction. These optional operations are now described in more detail below.

As described above, one or more liquid phases may be present when digesting cellulosic biomass solids. Particularly when cellulosic biomass solids are fed continuously or semi-continuously to the hydrothermal (hydrocatalytic) digestion unit, digestion of the cellulosic biomass solids may produce multiple liquid phases in the hydrothermal digestion unit. The liquid phases may be immiscible with one another, or they may be at least partially miscible with one another. In some embodiments, the one or more liquid phases may comprise a phenolics liquid phase comprising lignin or a product formed therefrom, an aqueous phase comprising the alcoholic component, a light organics phase, or any combination thereof. The alcoholic component being produced from the cellulosic biomass solids may be partitioned between the one or more liquid phases, or the alcoholic component may be located substantially in a single liquid phase. For example, the alcoholic component being produced from the cellulosic biomass solids may be located predominantly in an aqueous phase (e.g., an aqueous phase digestion solvent), although minor amounts of the alcoholic component may be partitioned to the phenolics liquid phase or a light organics phase. In various embodiments, the slurry catalyst may accumulate in the phenolics liquid phase as it forms, thereby complicating the return of the slurry catalyst to the cellulosic biomass solids in the manner described above. Alternative configurations for distributing slurry catalyst particulates in the cellulosic biomass solids when excessive catalyst accumulation in the phenolics liquid phase has occurred are described hereinafter.

Accumulation of the slurry catalyst in the phenolics liquid phase may, in some embodiments, be addressed by conveying this phase and the accumulated slurry catalyst therein to the same location where a fluid phase digestion medium is being contacted with cellulosic biomass solids. The fluid phase digestion medium and the phenolics liquid phase may be conveyed to the cellulosic biomass solids together or separately. Thusly, either the fluid phase digestion medium and/or the phenolics liquid phase may motively return the slurry catalyst back to the cellulosic biomass solids such that continued stabilization of soluble carbohydrates may take place. In some embodiments, at least a portion of the lignin in the phenolics liquid phase may be depolymerized before or while conveying the phenolics liquid phase for redistribution of the slurry catalyst. At least partial depolymerization of the lignin in the phenolics liquid phase may reduce the viscosity of this phase and make it easier to convey. Lignin depolymerization may take place chemically by hydrolyzing the lignin (e.g., with a base) or thermally by heating the lignin to a temperature of at least about 250° C. in the presence of molecular hydrogen and the slurry catalyst. Further details regarding lignin depolymerization and the use of viscosity monitoring as a means of process control are described in commonly owned United States Patent Application Publication US20140117275 and incorporated herein by reference in its entirety.

After forming the alcoholic component from the cellulosic biomass solids, at least a portion of the alcoholic component may be separated from the cellulosic biomass solids and further processed by performing a condensation reaction thereon, as generally described above. Processing of the alcoholic component that has partitioned between various liquid phases may take place with the phases separated from one another, or with the liquid phases mixed together. For example, in some embodiments, the alcoholic component in a fluid phase digestion medium may be processed separately from a light organics phase. In other embodiments, the light organics phase may be processed concurrently with the fluid phase digestion medium.

Optionally, the fluid phase digestion medium containing the alcoholic component may be subjected to a second catalytic reduction reaction external to the cellulosic biomass solids, if needed, for example, to increase the amount of soluble carbohydrates that are converted into the alcoholic component and/or to further reduce the degree of oxygenation of the alcoholic components that are formed. For example, in some embodiments, a glycol or more highly oxygenated alcohol may be transformed into a monohydric alcohol by performing a second catalytic reduction reaction. The choice of whether to perform a condensation reaction on a monohydric alcohol or a glycol may be based on a number of factors, as discussed in more detail below, and each approach may present particular advantages.

In some embodiments, a glycol produced from the cellulosic biomass solids may be fed to the condensation catalyst. Although glycols may be prone to coking when used in conjunction with condensation catalysts, particularly zeolite catalysts, the present inventors found the degree of coking to be manageable in the production of higher molecular weight compounds. Approaches for producing glycols from cellulosic biomass solids and feeding the glycols to a condensation catalyst are described in commonly owned United States Patent Application Publication US20140121420 and incorporated herein by reference in its entirety.

In some embodiments, a phenolics liquid phase formed from the cellulosic biomass solids may be further processed. Processing of the phenolics liquid phase may facilitate the catalytic reduction reaction being performed to stabilize soluble carbohydrates. In addition, further processing of the phenolics liquid phase may be coupled with the production of dried glycols or dried monohydric alcohols for feeding to a condensation catalyst. Moreover, further processing of the phenolics liquid phase may produce methanol and phenolic compounds from degradation of the lignin present in the cellulosic biomass solids, thereby increasing the overall weight percentage of the cellulosic biomass solids that may be transformed into useful materials. Finally, further processing of the phenolics liquid phase may improve the lifetime of the slurry catalyst.

These liquid phases or fluid phases can be used to remove water in the pretreatment as organic solvent, in the third contact zone, and thus be available for further processing Various techniques for processing a phenolics liquid phase produced from cellulosic biomass solids are described in commonly owned United States Patent Application Publications US20140121419, US20140117277, and US20140121418, each filed on Oct. 31, 2012 and incorporated herein by reference in its entirety. As described therein, in some embodiments, the viscosity of the phenolics liquid phase may be reduced in order to facilitate conveyance or handling of the phenolics liquid phase. As further described therein, deviscosification of the phenolics liquid phase may take place by chemically hydrolyzing the lignin and/or heating the phenolics liquid phase in the presence of molecular hydrogen (i.e., hydrotreating) to depolymerize at least a portion of the lignin present therein in the presence of accumulated slurry catalyst. Deviscosification of the phenolics liquid phase may take place before or after separation of the phenolics liquid phase from one or more of the other liquid phases present, and thermal deviscosification may be coupled to the reaction or series of reactions used to produce the alcoholic component from the cellulosic biomass solids. Moreover, after deviscosification of the phenolics liquid phase, the slurry catalyst may be removed therefrom. The catalyst may then be regenerated, returned to the cellulosic biomass solids, or any combination thereof.

In some embodiments, heating of the cellulosic biomass solids and the fluid phase digestion medium to form soluble carbohydrates and a phenolics liquid phase may take place while the cellulosic biomass solids are in a pressurized state. As used herein, the term "pressurized state" refers to a pressure that is greater than atmospheric pressure (1 bar). Heating a fluid phase digestion medium in a pressurized state may allow the normal boiling point of the digestion solvent to be exceeded, thereby allowing the rate of hydrothermal digestion to be increased relative to lower temperature digestion processes. In some embodiments, heating the cellulosic biomass solids and the fluid phase digestion medium may take place at a pressure of at least about 30 bar. In some embodiments, heating the cellulosic biomass solids and the fluid phase digestion medium may take place at a pressure of at least about 60 bar, or at a pressure of at least about 90 bar. In some embodiments, heating the cellulosic biomass solids and the fluid phase digestion medium may take place at a pressure ranging between about 30 bar and about 430 bar. In some embodiments, heating the cellulosic biomass solids and the fluid phase digestion medium may take place at a pressure ranging between about 50 bar and about 330 bar, or at a pressure ranging between about 70 bar and about 130 bar, or at a pressure ranging between about 30 bar and about 130 bar.

To facilitate a better understanding of the present invention, the following examples of preferred embodiments are given. In no way should the following examples be read to limit, or to define, the scope of the invention.

ILLUSTRATIVE EXAMPLES

Examples 1-5

Base Wash

A series of biomass pretreatment experiments were conducted in 15 mm or 25 mm diameter glass chromatography columns (Ace Glassware), with pretreatment solutions fed from glass buret via a Low-Flow Compact Metering Pump, 30 mL/min maximum, 115 VAC, from Cole Parmer (WU-07115-10). A retriever 500 fraction collector from Isco/Teledyne was used to collect sample fractions. Southeaster US pine wood was ground to a dimension of approximately 8 mm×3 mm×3 mm using a "Retsch Grinder" Model SM100 is a rotating knife blade grinder.

Samples of the feed wood, and wood following treatment were analyzed for metals via combustion, then dissolution of the resulting ash in sulfuric acid for analysis by plasma emission spectroscopy. A second sample was analyzed by ion chromatography to determine the chloride content of the wood samples.

Treatments for the biomass wash sequence entailed use of 0.5N KOH, deionized water, and 25% ethanol in deionized water.

The volume of the bed of wood treated was determined from the known column diameter, and the measured length of the wood bed, which was retained either via adjustable plungers, or silane treated glass wool plugs. Packing density for the ground wood samples ranged from 0.21 to 0.25 dry grams per milliliter of bed volume.

Results of the treatment experiments are tabulated in Table 1.

TABLE 1

Biomass pretreatment experiments

| Parameter | Units | Ex-1 | Ex-2 | Ex-3 | Ex-4 | Ex-5 |
|---|---|---|---|---|---|---|
| Flowrate | BV/h | 0.71 | 0.46 | 0.62 | 0.78 | 0.73 |
| 1% $H_2SO_4$ | BV | 0.00 | 0.28 | 0.99 | 0.14 | 0.00 |
| 0.5N KOH | BV | 0 | 0 | 0.99 | 0.14 | 0.26 |
| DI Water | BV | 3.39 | 2.20 | 0.99 | 2.48 | 2.33 |
| 25% EtOH | BV | 0.00 | 0.00 | 1.98 | 0.00 | 0.00 |
| Total BV | BV | 3.39 | 2.48 | 4.95 | 2.76 | 2.59 |
| Phosphorus | % remove | 32.2% | 22.0% | 100.0% | 100.0% | 100.0% |
| Manganese | % remove | −6.5% | 90.3% | 96.8% | 71.0% | −9.7% |
| Iron | % remove | 73.9% | 78.3% | 91.3% | 87.0% | 91.3% |
| Magnesium | % remove | 26.8% | 92.9% | 98.4% | 85.0% | 37.8% |
| Calcium | % remove | 48.1% | 92.9% | 98.3% | 86.9% | 51.9% |
| Chloride | % remove | 54.5% | 72.7% | 80.0% | 85.5% | 83.6% |

Comparison of Examples 1 and 2 where no base was used, vs. the other examples shows that base is important for removal of the chlorine and phosphorus, which are presumed to be ion exchanged into the wood matrix. The amount of base used to treat the wood could be very small, followed by waster wash to flush the base zone through the bed. Base addition was effective in removing phosphorous and improved the removal of chloride, as evidence in Examples 3 through 5.

Example 6

Solvent Drying

A 15 mm inside diameter×24 inch glass chromatography column was charged with 23 inches of ground pine wood with moisture content of 52.4%, measured by drying of a sample in a vacuum oven overnight at 86° C. 39.6 grams of wood were charged. Ethanol (less than 1000 ppm $H_2O$) was charged as solvent to a feed buret. The solvent was flowed upflow through the column at 0.8 ml/min using a Low-Flow Compact Metering Pump, 30 mL/min maximum, 115 VAC, from Cole Panner (WU-07115-10). A retriever 500 fraction collector from Isco/Teledyne was used to collect sample fractions. Southeaster US pine wood was ground to a dimension of approximately 8 mm×3 mm×3 mm using a "Retsch Grinder" Model SM100 is a rotating knife blade grinder.

Samples were collected in 50 ml fractions (0.48 bed volumes [BV]), and analyzed by Karl Fisher titration for water content. At the end of 3.9 bed volumes of solvent wash, the cumulative water removed corresponded to 103% of the assessed water content of the initially charged wood. This result indicates virtual complete removal of water via use of ethanol as solvent, under the conditions described.

Example 7

Gas Displacement

A 15 mm glass chromatography column was packed to a bed length of 22.5 inches with ground wood. The column was subjected to 1% sulfuric acid, water, and 0.5N base wash, followed by a final water rinse. Approximately 60 ml of final aqueous phase was drained from the bed at the end of the treatment sequence, representing 59% of the total bed volume.

This example represents draining of interstitial liquid from a water-wet bed, to remove a substantial (greater than 50%) portion of the liquid used to push base wash through the bed. The drained water can be re-used for subsequent wash steps.

What is claim is:

1. A method for selective removal of chlorine and phosphorus from a cellulosic biomass solids, said method comprising a plurality of vessels:
   a. providing each of said vessels with one of detrimental species-containing cellulosic biomass solids;
   b. introducing a quantity of a base solution having a pH of greater than 9 from an inlet into a first vessel of said plurality of vessels containing said detrimental species-containing cellulosic biomass solids at a temperature in the range of about 0° C. to about 60° C.;
   c. repeating step (b) for a second vessel of said plurality of vessels;
   d. introducing a quantity of aqueous solution having a pH of at most 8 from an inlet into said first vessel of said plurality of vessels treated according to step (b) thereby discharging the basic water effluent;
   e. repeating step (d) for the second vessel of said plurality of vessels treated according to step (c);
   f. introducing a quantity of gas or organic solution from an inlet into the first vessel of said plurality of vessels treated according to step (d) and discharging the aqueous effluent;
   g. repeating step (f) for the second vessel of said plurality of vessels treated according to step (e);
   h. recycling at least a portion of the discharged aqueous effluent as a portion of the base solution;
   i. transferring at least a portion of the biomass treated according to steps (f) and (g) to a digestion and/or reaction vessel;
   j. wherein at least 2 of the vessels are undergoing at least one of the steps (b) through (i) at the same time; and
   k. wherein the amount of the total basic water effluent from the plurality of vessels is in the range of from about 3 parts to about 0.5 parts relative to about 1 part of detrimental species—containing cellulosic biomass solids (dry basis).

2. The method of claim 1 wherein steps (b), (d) ,(f) and (i) are repeated for n vessels where n is an integer from 2 to 20.

3. The method of claim 2 wherein n is an integer from 2 to 10.

4. The method of claim 3 wherein n is an integer from 3 to 6.

5. The method of claim 1 further adjusting the pH of at least a portion of the discharged aqueous effluent to a pH of greater than 9 by adding a base to the discharged aqueous solution prior to recycling as a portion of the base solution.

6. The method of claim 1 wherein the base solution comprises a base selected from sodium hydroxide, potassium hydroxide or ammonia.

7. The method of claim 1 wherein the base solution comprises a base in an amount of less than 5 Normal and at least 0.01 Normal.

8. The method of claim 1 wherein, in the digestion and/or reaction zone, the treated cellulosic biomass is contacted with a hydrothermal hydrocatalytic catalyst in the presence of hydrogen and a digestion solvent thereby producing an intermediate oxygenated product stream comprising oxygenated hydrocarbons and water; and at least a portion of the water is separated and recycled as the aqueous solution.

9. The method of claim 1 wherein, in the digestion and/or reaction zone, the treated cellulosic biomass is contacted with a hydrothermal hydrocatalytic catalyst in the presence of hydrogen and a digestion solvent thereby producing an intermediate oxygenated product stream; at least a portion of the oxygenated intermediate product stream is converted to a hydrocarbon product stream comprising hydrocarbons and water; and at least a portion of the water is separated and recycled as the aqueous solution.

10. The method of claim 9 wherein, the oxygenated intermediate product stream comprises oxygenated hydrocarbons and water, and at least a portion of the water is separated and recycled as the aqueous solution.

11. The method of claim 1 wherein the aqueous solution is in-situ generated.

12. The method of claim 1 wherein the gas is selected from the group consisting of air, hydrogen, nitrogen, steam, organic vapors, and mixtures thereof.

13. The method of claim 9 wherein the organic solvent is the digestion solvent.

14. The method of claim 9 wherein the organic solvent is in-situ generated.

\* \* \* \* \*